United States Patent [19]

Boyd et al.

[11] Patent Number: 5,785,707
[45] Date of Patent: Jul. 28, 1998

[54] TEMPLATE FOR POSITIONING INTERBODY FUSION DEVICES

[75] Inventors: Lawrence M. Boyd, Memphis; Eddie Ray, III, Cordova, both of Tenn.

[73] Assignee: SDGI Holdings, Inc., Wilmington, Del.

[21] Appl. No.: 889,473

[22] Filed: Jul. 8, 1997

Related U.S. Application Data

[62] Division of Ser. No. 427,432, Apr. 24, 1995, Pat. No. 5,645,549.

[51] Int. Cl.$^6$ .............. A61B 17/36; A61B 17/58; A61F 2/00
[52] U.S. Cl. .............. 606/41; 606/45; 606/96
[58] Field of Search .............. 600/205; 606/37, 606/45–50, 96, 184–185, 190, 191, 198; 623/17

[56] References Cited

U.S. PATENT DOCUMENTS

| | | | |
|---|---|---|---|
| 3,848,601 | 11/1974 | Ma et al. | 606/61 |
| 3,964,480 | 6/1976 | Froning | 606/61 |
| 4,570,624 | 2/1986 | Wu | 606/96 |
| 4,721,116 | 1/1988 | Schintgen et al. | 606/185 |
| 4,772,287 | 9/1988 | Ray et al. | 623/17 |
| 4,877,020 | 10/1989 | Vich | 606/86 |
| 4,907,577 | 3/1990 | Wu | 606/87 |
| 5,112,236 | 5/1992 | Krevolin et al. | 606/96 |
| 5,133,720 | 7/1992 | Greenberg | 606/96 |
| 5,195,505 | 3/1993 | Josefsen | 606/198 |

*Primary Examiner*—Randy C. Shay
*Attorney, Agent, or Firm*—Woodard, Emhardt, Naughton, Moriarty & McNett

[57] ABSTRACT

A template assembly is provided for marking locations on the disc annulus for the implantation of an interbody fusion device or the introduction of a working instrument. The template assembly includes a tubular body sized for percutaneous introduction into a patient and advancement to an affected intervertebral disc. An elongated shaft slidably extends through the tubular body and is threadedly engaged to the tubular body at its proximal end so that rotation of the shaft relative to the tubular body advances the shaft through the body. A guide foot is pivotably connected to the distal end of the tubular body to be pivoted from a first position aligned with the tubular body to a second deployed position oriented substantially perpendicular to the tubular body. The guide body is pivoted from the first position to the second position by advancement of the elongated shaft through the tubular body. The guide body in one embodiment defines a bore through which the working tip of an electrocautery instrument extends to mark the disc annulus. In another embodiment, the guide body itself defines an electrocautery projection. The template assembly can be anchored to the affected disc by a guide wire extending through the tubular body and about which the template assembly can be rotated to make an additional mark on the annulus at a predetermined distance from the first mark.

6 Claims, 5 Drawing Sheets

TEMPLATE FOR POSITIONING INTERBODY FUSION DEVICES

This application is a division of application Ser. No. 08/427,432, filed Apr. 24, 1995 which issued on Jul. 8, 1997 as U.S. Pat. No. 5,645,549.

The present invention relates to a template to facilitate proper positioning of an implant into the intradiscal space between adjacent vertebrae. The template of this invention is particularly useful in connection with interbody fusion devices, especially of the type shown and described in pending application Ser. No. 08/411,017, filed on Mar. 27, 1995, owned by the assignee of the present invention and naming common inventors.

One of the most common sources of low back pain is damage or defects in the spinal disc separating adjacent vertebrae. The disc can be herniated or suffering from a variety of degenerative conditions, so that in either case the anatomical function of the spinal disc is disrupted. In recent years the most prevalent treatment for these types of conditions has been to fuse the two adjacent vertebrae together, thereby eliminating the normal movement of the affected disc. Depending upon the condition of the disc, the entire disc may be removed, or the disc annulus can be left intact with some or all of the disc nucleus removed.

Figure 1:
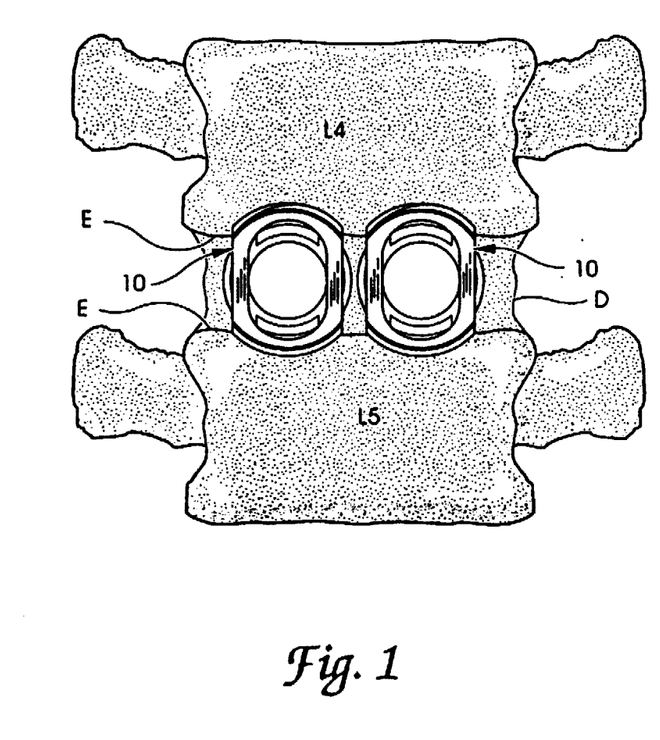
FIG. 1 is an elevational view of the anterior aspect of the L4-L5 motion segment shown instrumented with a pair of interbody fusion devices.
Figure 2:
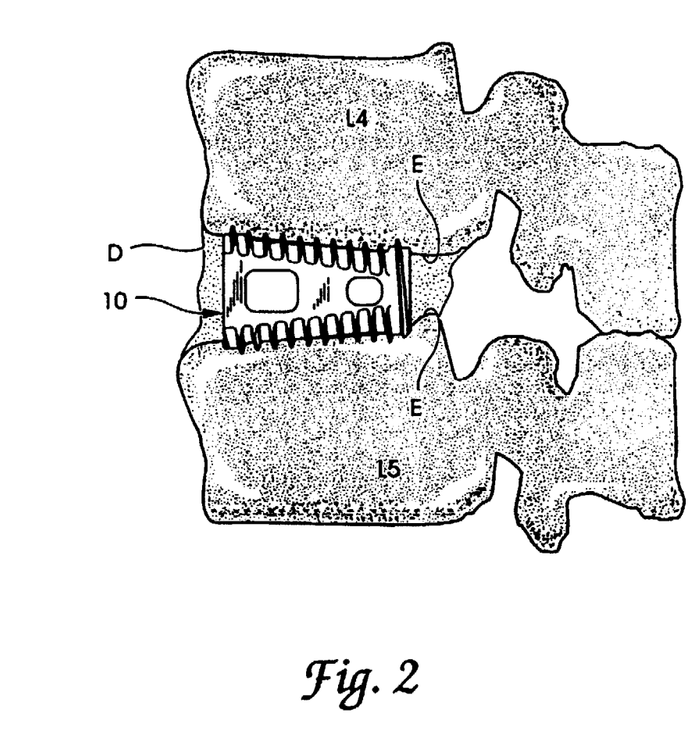
FIG. 2 is a side elevational view of the motion segment and fusion device construct depicted in FIG. 1.

With the removal of the disc or disc nucleus, something is required in the intradiscal space to maintain the normal anatomic position of the adjacent vertebrae, at least until fusion occurs. One common device for maintaining the disc space is the interbody fusion device. In one type of interbody fusion device, multiple such implants are disposed between the adjacent vertebrae, separated by space to receive bone graft material. An example of one such device is found in the above-mentioned co-pending application, Ser. No. 08/411,017, entitled INTERBODY FUSION DEVICE AND METHOD FOR RESTORATION OF NORMAL SPINAL ANATOMY, filed on Mar. 27, 1995, which disclosure and figures are-incorporated by reference. Bilateral placement of two such fusion devices is depicted in FIGS. 1 and 2. The device 10 is tapered to maintain the normal curvature of the vertebral level (L4–L5), and is threaded for engagement with the vertebral endplates E. The device 10 can be implanted through portals formed in the disc annulus D. As illustrated in FIGS. 1 and 2, two fusion devices 10 are implanted to fill-the disc space, effectively maintain the spinal curvature and provide adequate space between the-implants to be filled with bone graft material.

In the operative procedure for implanting the fusion device, a midline incision is made to expose the anterior aspect of the. vertebral bodies at least one level above and below the affected motion segment. The soft tissues are denuded at the target disc to provide adequate space to implant the fusion device. Placement and positioning of the fusion device is typically assessed under direct vision, and the depth of insertion of the device assessed through lateral x-ray.

One difficulty with current techniques for implanting multiple implants arises in determining the proper position for the implants to avoid interference between the implants within the disc space and to maintain adequate spacing between the implants to receive bone graft material. There is a need for a simple device, or template, that can be easily used by the spinal surgeon to determine the optimum position for implanting a fusion device. In U.S. Pat. No. 4,772,287 to Dr. Charles Ray et al., a posterior technique is described in which holes are drilled through each of the facet joints to provide a window for insertion of prosthetic disc capsules. Although in this technique the windows act as a guide for the insertion instruments, the size and orientation of these guide windows is severely limited by the facet joint itself. For example, in the '287 Patent, the holes through the facet joints are 11-mm. which is an appropriate size for the smaller implant described in that patent. However, larger implants, such as that described in the above-mentioned co-pending application, cannot fit through the same small hole, and instead require complete removal of the facet joint. Moreover, since the technique described in the '287 relies upon the facet joint as a guide, it cannot be implemented in an anterior approach. Thus, the surgical approach described in this Ray patent cannot be used to implant the anterior fusion devices disclosed in the above-mentioned co-pending application Ser. No. 08/411,017.

Another approach as described in U.S. Pat. No. 3,964,480, to Froning, is to use a stereotactic fixture to-align instruments puncturing the disc annulus. The '480 Patent describes the use of this fixture to provide unobstructed puncture of the intervertebral disc for injection of fluids, such as radiographic contrast fluids and decompression drugs, such as chymopapain. However, as is evident from the figures of the '480 Patent, the described stereotactic fixture is large and unwieldy, and certainly does not lend itself well as a simple device for determining the position for implantation of a fusion device. In addition, the stereotactic fixture in the '480 patent is not suited for approaching the disc space anteriorly.

The need of spinal surgeons for a device for positioning of multiple implants within the intervertebral space is not adequately met by any of these prior devices or techniques. This need is magnified when such implants are placed via trocars and video-assisted spinal surgery methods, where exposure of the disc space is more difficult and accurate surgical orientation more critical. What is needed is a simple and easily used template that allows a surgeon to readily locate where an implant should be inserted into the intradiscal space.

SUMMARY OF THE INVENTION

This unresolved need is met by the template assembly of the present invention. In one embodiment, the template assembly comprises a tubular body sized for percutaneous introduction into the human body, and particularly for introduction to the disc annulus. The tubular body has a proximal end residing outside the patient and a distal end residing adjacent the disc annulus when the template is in use. The template assembly further comprises an elongated guide foot pivotably connected to the distal end of the tubular body by a hinge. The guide foot initially assumes a first retracted position in which the foot is aligned with the longitudinal axis of the tubular body to facilitate introduction of the template via a seal or working channel anchored to the skin. The guide foot is pivotable to a second deployed position in which the foot is oriented at an angle relative to the longitudinal axis of the tubular body. In this position, the guide foot can rest against the disc annulus.

The template assembly includes an elongated deployment shaft sized to slidably extend through the tubular body to project beyond the distal end of the body. The deployment shaft has a generally rounded or blunt distal tip to bear against the guide foot as the shaft is pushed through the tubular body. In particular, as the shaft is-advanced through the body, the rounded tip pushes against the guide foot to cause the foot to pivot about the hinge from the guide foot's first position to its second deployed position. To ensure a controlled deployment of the guide foot, the elongated shaft is threadedly engaged to the tubular body so that rotation of the shaft relative to the tubular body achieves controlled advancement of the shaft through the body. A handle at the proximal end of the deployment shaft provides adequate purchase for the surgeon to rotate the shaft.

In one embodiment of the inventive template assembly, the guide foot includes a guide bore extending therethrough. The guide bore is sized to receive the operative end of a marking instrument, such as the working tip of an electrocautery device. In use, the template assembly is initially introduced, preferably percutaneously, into the spinal space at the affected vertebral level. During initial introduction, the deployment shaft is retracted into the tubular body and the guide foot is oriented in its first position aligned with the longitudinal axis of the body, thereby presenting the smallest profile possible. When the distal end of the tubular body is near the disc annulus, the deployment shaft is advanced through the tubular body to gradually push the guide foot to its pivoted second position.

With the guide foot in its deployed position, the elongated shaft can be removed from the tubular body to permit introduction of a guide wire through the body. The guide wire is used to puncture the disc annulus and provide an anchor and a pivot point for the template assembly. With the guide wire firmly engaged in the spinal disc the guide foot is moved into contact with the disc annulus. An electrocautery instrument is then introduced with its tip extending through the guide bore in-the foot. The energized tip cauterizes the disc annulus, thereby marking the proper position for insertion of an interbody fusion device. The template assembly is then pivoted about the anchored guide wire so that the guide foot is positioned at the opposite side of the disc annulus. A second mark is made with the electrocautery instrument through the guide bore to denote the position for insertion of a second fusion device. The guide wire and template assembly can then be removed. As the template assembly is removed, the tissue surrounding the surgical site will push against the guide foot causing it to pivot back to its first position aligned with the tubular body.

In a second embodiment, the guide foot does not include a guide bore, but instead includes a feature for itself marking the disc annulus. The guide foot can include a projection from the surface facing the disc that serves as an electrocautery tip. The template assembly includes an electrical connection for providing electrical energy to the projection of the guide foot.

One object of the present invention is to provide a template to facilitate accurate positioning of implants within the intradiscal space. A further object resides in features of the invention that permit percutaneous introduction and use of the template assembly. Yet another object is to provide a template assembly that can be easily used to mark the disc annulus, and that can be easily and quickly removed afterwards.

One important benefit of the template assembly of the present invention is that it provides the surgeon with an accurate mark for positioning multiple implants within the intradiscal space. Another benefit is that the template assembly can be readily adapted to accommodate different sizes of implants and readily oriented to mark different locations around the disc annulus.

Other objects and benefits of the inventive template assembly will become apparent upon consideration of the following description of the invention and the accompanying figures.

DESCRIPTION OF THE PREFERRED EMBODIMENTS

For the purpose of promoting an understanding of the principles of the present invention, reference will be made to the embodiments illustrated in the accompanying drawings and specific language will be used to describe the same. It is understood that the specific language and figures are not intended to limit the scope of the invention only to the illustrated embodiment. It is also understood that alterations or modifications to the invention or further application of the principles of the invention are contemplated as would occur to persons of ordinary skill in the art to which the invention relates.

Figure 3:
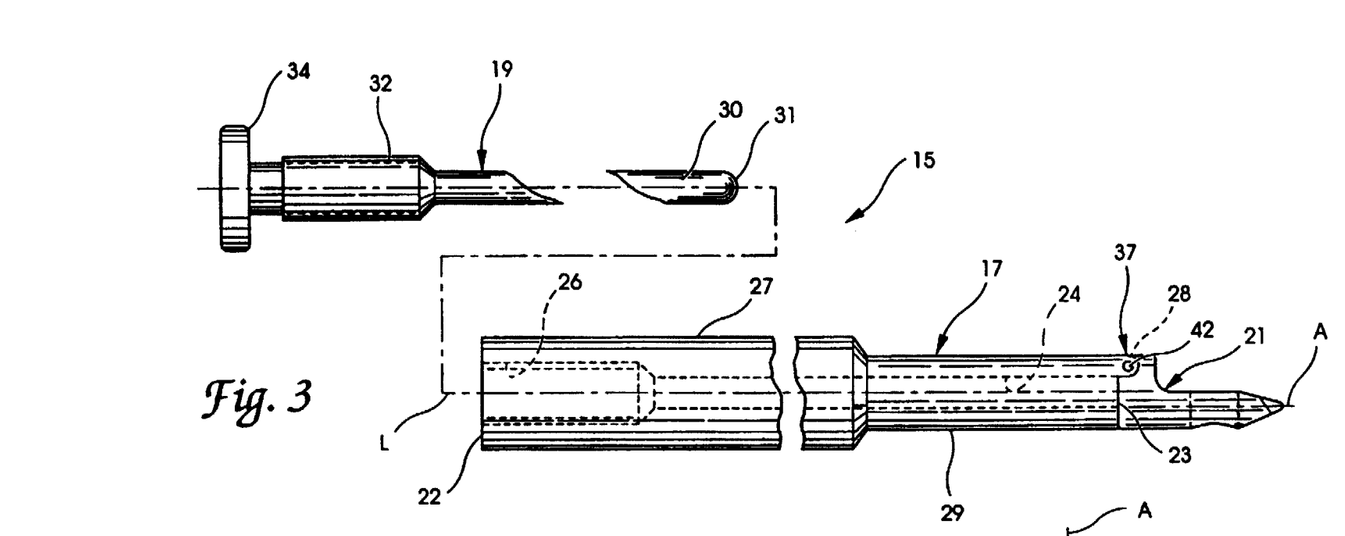
FIG. 3 is an exploded view of the components of the template assembly according to one embodiment of the present invention.

Referring now to FIG. 3, a template assembly 15 in accordance with a preferred embodiment of the invention is illustrated. The template assembly 15 includes an outer tubular body 17, an inner deployment shaft 19 and a guide foot 21. The tubular body 17 is elongated along a longitudinal axis L between its proximal end 22 and its distal end 23. In use, the proximal end 22 is disposed outside the skin of the patient while the distal end 23 is situated adjacent the disc annulus of the affected motion segment.

The tubular body 17 defines a central bore 24 from end to end to slidably receive the deployment shaft 19. At the proximal portion 27 of the tubular body 17, the central bore 24 includes a threaded bore 26. The proximal portion 27 is larger than the distal portion 29 of the tubular body 17, primarily to provide a smaller profile in the region of the vertebrae. In addition, the larger diameter of the proximal portion 27 provides a better grip for the spinal surgeon manipulating the template assembly 15 in situ. The deployment shaft 19 includes an elongated probe 30 configured to project beyond the distal end 23 of the tubular body 17 and having a generally rounded or blunt tip 31 for reasons set forth below. At the proximal end of the deployment shaft 19 is a threaded portion 32 having threads that mate with the threaded bore 26 of the tubular body 17. The proximal end of the deployment shaft is configured into a handle or knob 34 adapted to facilitate rotation of the deployment shaft 19 within the tubular body 17. The knob 34 is preferably circular with knurling or other gripping feature defined on the circumference of the knob to facilitate manual rotation of the knob.

Figure 4:
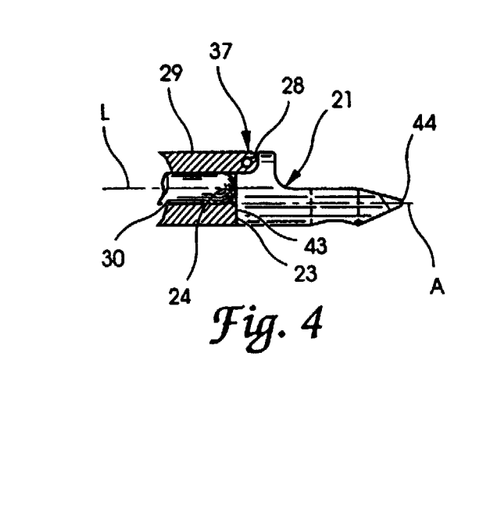
FIG. 4 is an enlarged partial cross-sectional view of the distal tip of the template assembly illustrated in FIG. 3, shown with the guide foot in its initial insertion position.
Figure 6:
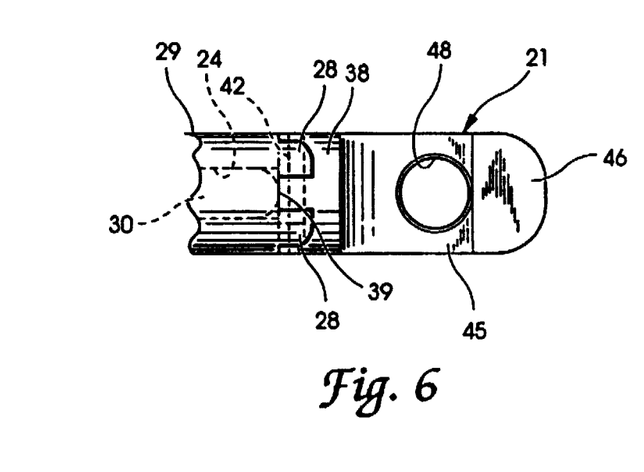
FIG. 6 is a partial top elevational view of the distal tip of the template assembly as illustrated in FIG. 4.
Figure 7:
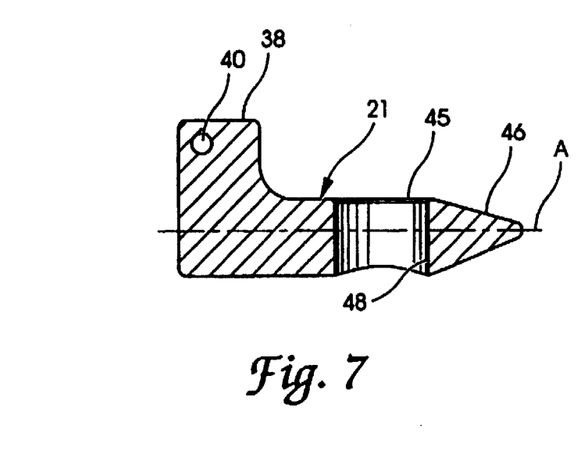
FIG. 7 is a side cross-sectional view of the guide foot.

Details of the guide foot 21 and its connection to the tubular body 17 can be discerned from FIGS. 7–10. In particular, the guide foot 21 includes a hinge portion 38 and a guide portion 45, with the portions preferably oriented at right angles so that the guide foot takes on the shape of an "L", as seen in FIG. 7. The hinge portion 38 of the guide foot defines a hinge boss 39 that is disposed between a pair of hinge flanges 28 projecting from the distal end 23 of the tubular body 17, as best seen in FIGS. 4 and 6. A hinge pin 42 passes through bores in the hinge flanges 28 and a hinge bore 40 defined in the hinge boss 39 of the guide foot.

Figure 8:
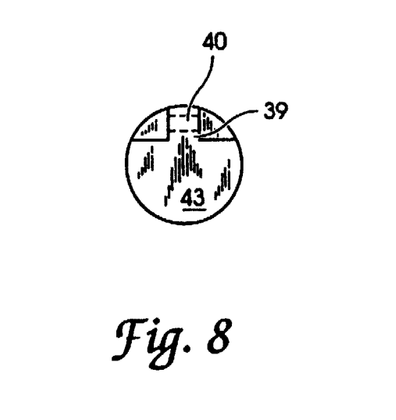
FIG. 8 is an end elevational view of the proximal end of the guide foot.
Figure 9:
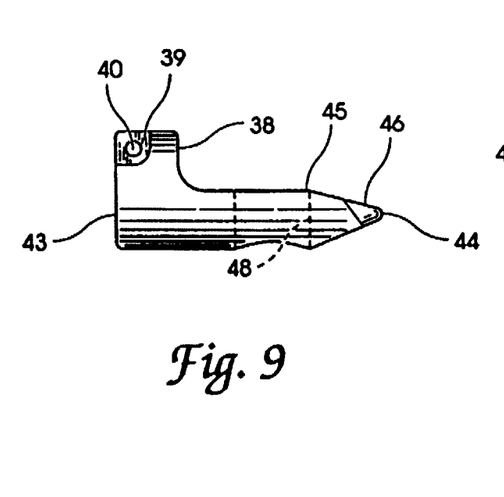
FIG. 9 is a side elevational view of the guide foot.
Figure 10:
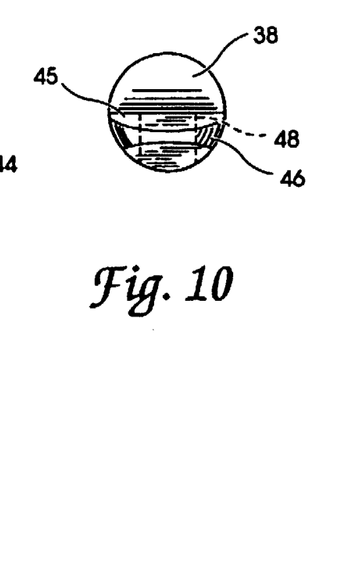
FIG. 10 is an end elevational view of the distal end of the guide foot.

The hinge portion 38 of the guide foot 21 defines a proximal face 43 that is closely adjacent the distal end 23 of the tubular body when the guide foot is in its first retracted position shown in FIGS. 3–4. In this first position the axis A of the guide portion 45 of the guide foot is aligned with the longitudinal axis L of the tubular body. The guide foot 21, and particularly the hinge portion 38, is circular in profile, as depicted in FIG. 8, with an effective outer diameter substantially equal to or less than the outer diameter of the tubular body 17. Thus, the guide foot 21 presents a profile that is no larger than the tubular body, which is a beneficial feature for percutaneous introduction of the template assembly 15. The guide portion 45 of the guide foot also includes a tapered tip 46 at its distal end 44 to reduce the risk of trauma to the tissue at the surgical site during introduction of the template assembly.

Figure 5:
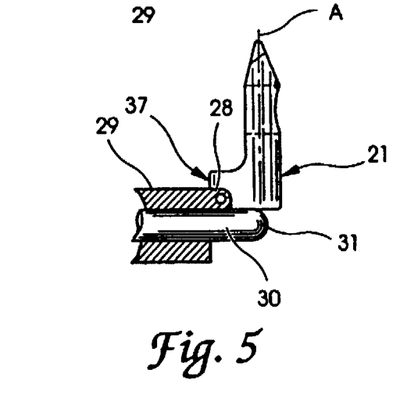
FIG. 5 is an enlarged partial cross-sectional view of the distal tip as illustrated in FIG. 4, shown with the guide foot in its second deployed position.

As can be seen in FIGS. 3–5 the guide foot 21 is pivotably connected to the tubular body 17 at the hinge 37. The hinge 37 is offset to one side of the tubular body to take advantage of the "L" shape of the guide foot 21. The guide foot 21 initially assumes its first position, shown in FIGS. 3–4, in which the axis A of the guide portion 45 of the guide foot is aligned with, and preferably parallel to, the longitudinal axis L of the tubular body 17. The guide foot 21 is pivotable to its second deployed position in which the axis A of the foot is at an angle, preferably perpendicular, to the longitudinal axis L, as shown in FIG. 5. The guide foot 21 is pushed from the first position of FIG. 4 to its second position of FIG. 5 by the rounded tip 31 of the elongated probe 30.

The guide portion 45 of the guide foot 21 includes a guide bore 48 defined therethrough. The guide bore 48 is sized to receive the working tip of a marking instrument. Preferably, the marking instrument is an electrocautery instrument that cauterizes the disc annulus. The marking instrument must be capable of leaving a mark on the annulus sufficient to be visually observed by the spinal surgeon. This mark will identify the proper position for inserting an implant into the disc space. Typically, the annulus will be fenestrated at the mark in order to receive an interbody fusion device, such as the device described above.

Steps in the use of the template assembly 15 are depicted in FIGS. 11a–13b. In the first step, the patient's skin S is punctured to receive a sealed trocar 50. The trocar 50 optimally provides a working channel for the template assembly 15, as well as for diskectomy instrumentation, fusion devices and insertion instrumentation to be used subsequently. One significant advantage achieved by the template assembly 15 according to this invention is that it is well suited for use in percutaneous endoscopic procedures. It has been found that diskectomies and even fusions can be performed using minimally invasive techniques, without the necessity of the more difficult and invasive surgical procedures of the past.

Figures 11A, 11B, 12A, 12B, 13A, 13B:
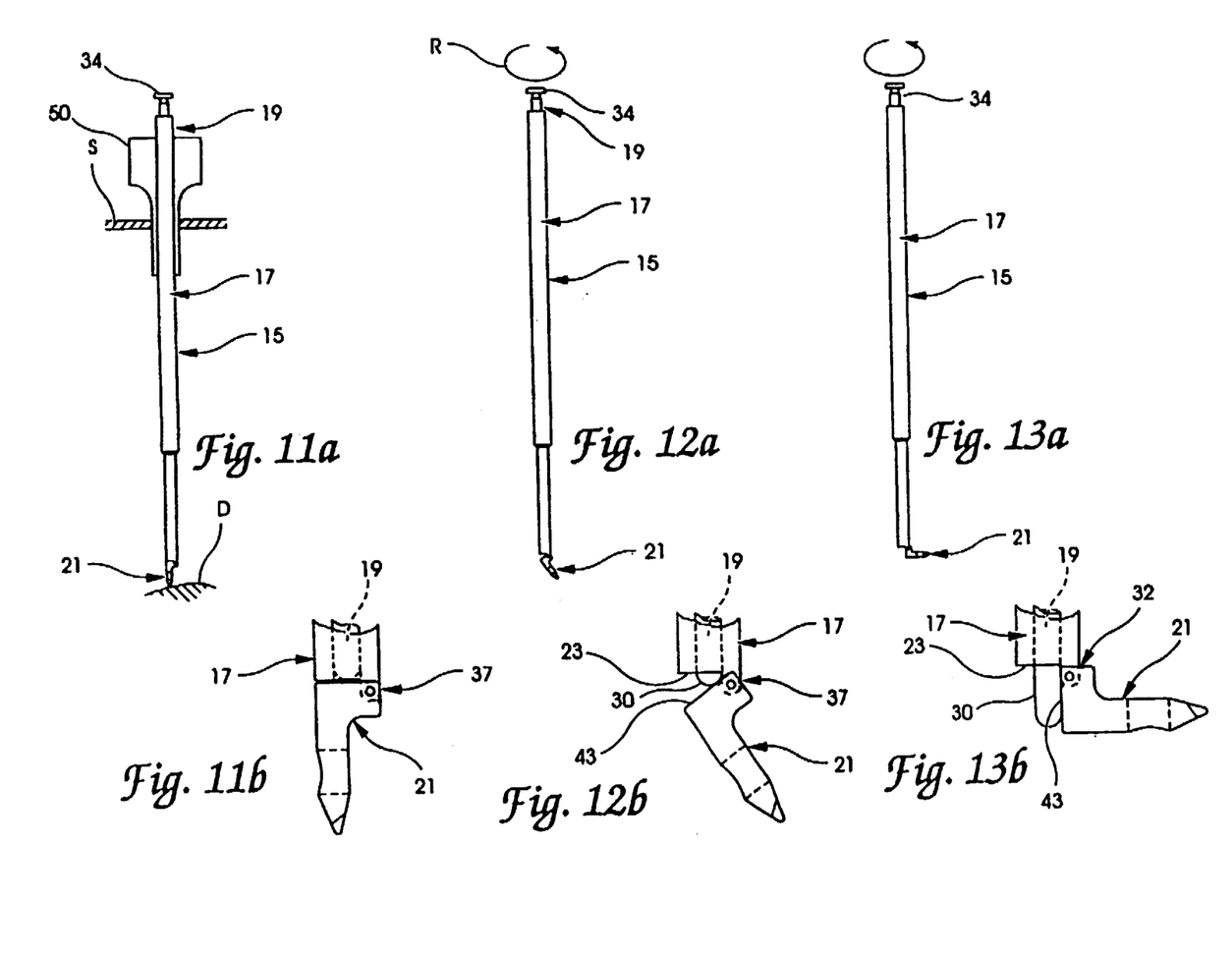
FIGS. 11a-11b are pictorial representations of the template assembly percutaneously inserted into the patient.
FIGS. 12a-12b are pictorial representations of the template assembly as the guide foot is being deployed.
FIGS. 13a-13b are pictorial representations of the template assembly with the guide foot fully deployed.

With the sealed trocar 50 anchored to the skin S, the template assembly 15 is introduced with the guide foot 21 in its first position, as depicted in FIG. 11b. The deployment shaft 19 is retracted within the tubular body 17 during this step so that the rounded tip 31 does not project beyond the distal end 23 of the body. Once the guide foot 21 contacts the disc annulus D the template assembly 15 is withdrawn slightly to allow the guide foot to be pushed and pivoted to its second position. The deployment shaft 19 is advanced through the tubular body 17 by rotating the knob 34 in the direction R shown in FIG. 12a. As the knob 34 and deployment shaft 19 is rotated, the probe 30 bears against the proximal face 43 of the guide foot 21 to cause the foot to pivot about the hinge 37. As the probe 30 moves farther beyond the distal end 23 of the tubular body 17, the guide foot pivots progressively through the position shown in FIG. 12b to its second fully deployed position shown in FIG. 13b.

Figure 14:
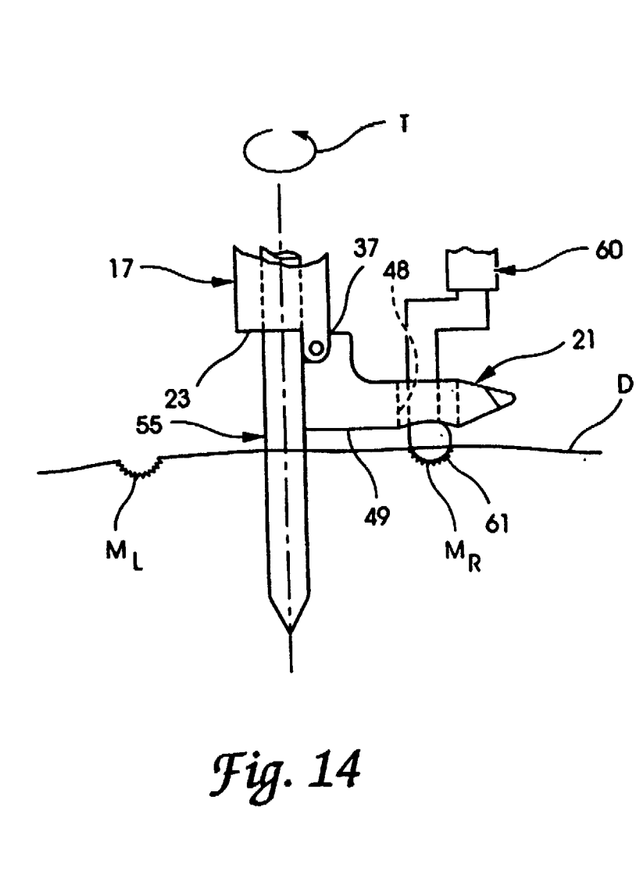
FIG. 14 is an enlarged pictorial representation of the template assembly anchored to the disc and showing the use of an electrocautery instrument in connection with the deployed guide foot for marking the disc annulus.

With the guide foot 21 in its second position, the template assembly 15 is advanced toward the disc until the bottom surface 49 of the foot is against the disc annulus D. The deployment shaft 19 can be removed and replaced with a guide wire 55, as shown in FIG. 14. The guide wire has a sharp tip to pierce the disc annulus D and may include means to limit and control advancement of the guide wire into the disc. The guide wire is advanced into the disc a sufficient distant to effectively anchor the template assembly 15 in position with the guide foot 21 in contact with the annulus D. An electrocautery instrument 60 is then introduced to the surgical site so that the working tip 61 extends through the guide bore 48 in the guide foot 21. The working tip 61 is energized to cauterize the disc annulus D leaving a mark MR on the annulus. This mark MR is visible to the surgeon to identify the proper location for insertion of an implant into the disc space. With the guide wire 55 still anchored in the disc, the entire template assembly 15.can be pivoted about the guide wire in the direction T shown in FIG. 14. The guide foot 21 is then oriented on the left side of the guide wire, on the opposite side of the disc from the first mark MR. A second mark ML can then be made on the disc annulus D using the electrocautery instrument. Once all the necessary marks are made on the disc annulus, the guide wire can be withdrawn, followed by the template assembly 15. As the assembly is withdrawn from the surgical site, the surrounding tissue bears against the guide foot 21 to cause it to pivot about the hinge 37 and return to its first low-profile position.

Figure 15:
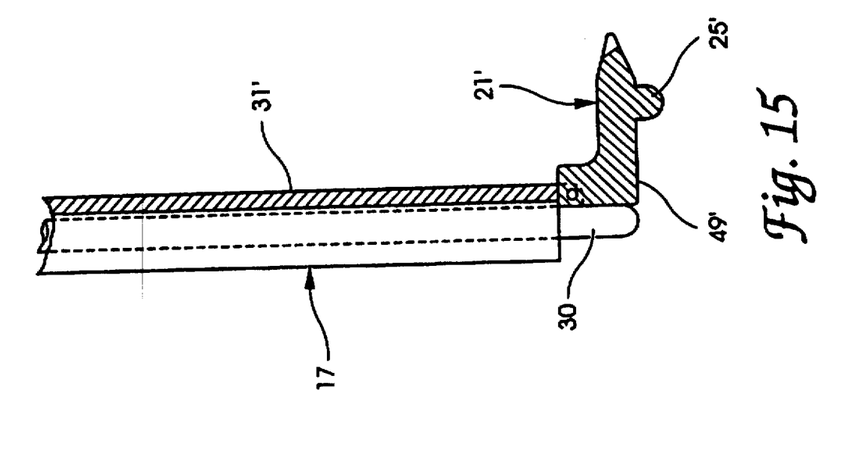
FIG. 15 is a side elevational view of another embodiment of the template assembly in which the guide foot carries an electrocautery projection for marking the disc annulus.

In an alternative embodiment, shown in FIG. 15, the guide foot 21' is modified from the foot 21 shown in FIG. 14. Specifically, the guide bore 48 is eliminated in favor of an electrocautery projection 25' formed in the bottom surface 49' of the guide foot. An electrical attachment 31' provides electrical energy to the guide foot 21'. In this instance, the guide foot 21' is formed of an electrically conductive material and the projection 25' is configured to emulate the working tip of an electrocautery instrument. One benefit of this configuration is that it is not necessary to introduce a separate electrocautery instrument to the surgical site.

The components of the template assembly 15 are sized for percutaneous introduction to the disc. In one specific embodiment, the assembly has an overall length of 12.5 in.(31.75 cm) from the proximal end 22 of the tubular body 17 to the distal end 44 of the guide foot 21 in its retracted first position. The tubular body 17 has an outer diameter in the specific embodiment of about 0.437 in. (1.11 cm) at the proximal portion 27 and of about 0.250 in. (1.74 cm) at the distal portion 29. The central bore 24 of the tubular body 17 has a diameter of 0.125 in. (0.87 cm), while the deployment shaft has a diameter of 0.120 in. (0.30 cm) to be slidably disposed within the central bore. The mating threads between the deployment shaft 19 and the tubular body 17 are preferably ¼–20 UNC-2B threads.

In one specific embodiment, the guide foot 21 has an effective outer diameter of 0.250 in. (1.74 cm) and a length from proximal face 43 to the distal end 44 of 0.541 in. (1.37 cm). The guide bore 48 has a diameter of 0.136 in. (0.35 cm) with its center being located 0.313 in. (0.80 cm) from the proximal face 43. The distance to the center of the guide bore 48 establishes the spacing between the two marks MR and ML made on the disc annulus D to identify the location for insertion of the fusion implants. Referring again to FIG. 14, it can be seen that the mark MR is made at predetermined distance from the guide wire 55 anchored in the disc. When the template assembly is pivoted about the guide wire, the mark ML is separated from the mark MR by twice that predetermined distance. This distance between marks is determined by the necessary separation between the interbody fusion devices to be introduced into the intradiscal space. In the specific illustrated embodiment, the fusion devices may have a maximum diameter of about 0.787 in. (2.00 cm), which requires the two marks MR and ML to be at least that distance apart.

In the illustrated embodiments, the template assembly is configured to mark the location for insertion of two bilateral fusion devices in the lower lumbar spine. Naturally, the dimensions of the guide foot 21 and the guide bore 48, or cauterizing projection 25', will be reduced in accordance with the geometry of the spinal anatomy at the affected motion segment. In addition, the template assembly can be configured to provide guide marks for the implantation of more than two fusion devices. In procedures involving three or more such devices, the template assembly can be oriented over successively made marks with the guide wire anchored into the disc at the marks. New marks can be made in-the described fashion by pivoting the template assembly about the guide wire. The distance to the center of the guide bore 48 or cauterization projection 25' would be reduced accordingly.

The invention has been illustrated and described in detail in the foregoing description and accompanying drawings, which are intended to be illustrative but not restrictive in character. It is of course understood that only the preferred embodiments have been shown and that all changes and modifications that fall within the spirit of the invention are desired and contemplated to be protected.

For example, the template assembly 16 has been described as used with a separate guide wire 55 to anchor and orient the assembly during the marking steps. In the illustrated embodiments, the deployment shaft 19 was required to be removed to accommodate the guide wire 55. Alternatively, the deployment shaft can be cannulated to receive the guide wire therethrough. In this embodiment, the deployment shaft need not be removed. The rounded tip 31 of the deployment shaft will not traumatize the disc annulus. The diameter of the deployment shaft is sufficient to accept a thin guide wire.

The guide foot 21 has been described and depicted as having an "L" shape. Other configurations are contemplated by this invention, provided that the guide bore or cauterization projection can be maintained at the predetermined distances discussed above. In accordance with the present invention, the components are contemplated to be formed from surgical grade stainless steel or other medically suitable material. The guide foot can be composed of a plastic material to minimize heat conduction from the working tip of the electrocauterization instrument. Alternatively, the device may be fabricated of a radioluscent plastic or composite material to allow unimpeded viewing of the guide wire placement and anatomical orientation. Other suitable materials for the components of the template assembly 15 are contemplated.

While the invention has been described for use in positioning bilateral fusion devices, the same marking capability can be used for other procedures. For example, the template can be used to mark the location for insertion of various instruments and tools into the disc space. Other uses for the template assembly 15 of the present invention may readily present themselves to persons of ordinary skill in this art.

What is claimed is:

1. A template assembly to facilitate the placement of an implant or instrument at a portion of the spine, such as the disc space between adjacent vertebrae, comprising:

a tubular body sized for introduction into a patient for advancement to the portion of the spine, said tubular body having a longitudinal axis, and a proximal end disposed outside the patient and a distal end disposed adjacent the portion of the spine when said body is within the patient;

an elongated guide foot having an axis, said guide foot being pivotably connected to said tubular body at a hinge disposed at said distal end, whereby said guide foot is pivotable between a first position in which said axis is parallel to said longitudinal axis of said tubular body for introduction into the patient, and a second position in which said axis is oriented at an angle relative to said longitudinal axis of said tubular body; and deployment means extending through said tubular body and operating on said guide foot for causing said guide foot to pivot about said hinge between said first position and said second position, wherein said guide foot includes marking means associated therewith for creating a mark on the disc annulus identifying a location on the annulus, said marking means including;

a projection defined on a surface of said guide foot oriented adjacent the disc annulus when said guide foot is in said second position; and means for providing electrical energy to said projection to heat said projection for cauterizing the disc annulus.

2. The template assembly according to claim 1, wherein said projection is substantially spherical.

3. The template assembly according to claim 1, wherein said means for providing electrical energy includes:

said guide foot and said projection being formed of an electrically conductive material; and an electrical attachment connected to said guide foot and extending along the length of said tubular body for engagement to a source of electrical energy outside the patient.

4. The template assembly according to claim 1, wherein said guide foot is L-shaped with a hinge portion connected to said tubular body and a guide portion oriented substantially perpendicular thereto with said guide portion defining said axis of said guide foot.

5. The template assembly according to claim 1, wherein said guide foot is tapered at an end of said guide foot distal from said hinge.

6. The template assembly according to claim 5 wherein said projection is defined adjacent said end of said guide foot.

* * * * *